US012767681B2

(12) United States Patent
Mano et al.

(10) Patent No.: US 12,767,681 B2
(45) Date of Patent: Oct. 20, 2026

(54) ENZYMATIC MODIFICATION OF LIGNIN FOR SOLUBILIZATION THEREOF, AND USES

(71) Applicant: CENTRE NATIONAL DE LA RECHERCHE SCIENTIFIQUE, Paris (FR)

(72) Inventors: Nicolas Mano, Talence (FR); Sébastien Gounel, Berthez (FR); Wilfrid Neri, Les Peintures (FR); Alain Derre, Balizac (FR); Philippe Poulin, Talence (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 999 days.

(21) Appl. No.: 16/756,016

(22) PCT Filed: Oct. 16, 2018

(86) PCT No.: PCT/EP2018/078244

§ 371 (c)(1),
(2) Date: Jul. 8, 2020

(87) PCT Pub. No.: WO2019/076893

PCT Pub. Date: Apr. 25, 2019

(65) Prior Publication Data

US 2020/0407388 A1 Dec. 31, 2020

(30) Foreign Application Priority Data

Oct. 16, 2017 (FR) ...................................... 17 59682

(51) Int. Cl.

*C07G 1/00* (2011.01)
*C12P 19/04* (2006.01)
*D01D 1/02* (2006.01)
*D01D 5/06* (2006.01)
*D01F 9/17* (2006.01)

(52) U.S. Cl.

CPC ................ *C07G 1/00* (2013.01); *C12P 19/04* (2013.01); *D01D 1/02* (2013.01); *D01D 5/06* (2013.01); *D01F 9/17* (2013.01); *C12Y 103/03005* (2013.01)

(58) Field of Classification Search

CPC ........................................................ C07G 1/00
See application file for complete search history.

(56) References Cited

U.S. PATENT DOCUMENTS 3,461,082 A * 8/1969 Yoshihiko ................ D01F 9/17 502/436
6,072,015 A * 6/2000 Bolle ................ C09D 197/005 527/400
6,905,853 B1 * 6/2005 Wang ................ C11D 3/38654 435/6.12
10,626,553 B2 * 4/2020 Birikh .................. C08L 97/005
2001/0018956 A1 * 9/2001 Stohrer .................... C07G 1/00 162/76
2007/0164468 A1 * 7/2007 Buchert ................ D21H 15/10 264/134
2011/0263836 A1 * 10/2011 Vuorenpalo ........... D21C 9/005 162/76
2014/0120566 A1 * 5/2014 Mano ...................... C02F 3/342 435/189
2015/0037241 A1 * 2/2015 Lehmann .................. D01F 9/17 264/182
2017/0267816 A1 * 9/2017 Schober .................. C04B 24/24
2018/0162891 A1 * 6/2018 Miettinen ................ C07G 1/00
2019/0271112 A1 * 9/2019 Birikh .................... D21C 9/163
2022/0064200 A1 * 3/2022 Suonpää ........ C12Y 110/03002

FOREIGN PATENT DOCUMENTS

EP 2213678 A1 8/2010
EP 2535378 A1 12/2012
JP S47-035323 A 11/1972
JP S49-100328 A 9/1974
JP H05-336951 A 12/1993
JP 2002-356405 A 12/2002
JP 2004-043998 A 2/2004
JP 2009-114181 A 5/2009
JP 2014-523235 A 9/2014
WO WO-0068500 A1 * 11/2000 ............. D21H 21/20
WO 2011/117839 A1 9/2011
WO 2012/160517 A1 11/2012
WO 2017/017381 A1 2/2017

OTHER PUBLICATIONS

Tang et al. (BioMed Research International, vol. 2015, 14) (Year: 2015).*
Tang et al. , BioMed Research International, vol. 2015, 1-14 (Year: 2015).*
Hamalainen et al. (Frontiers in Bioengineering and Biotechnology, Mar. 2018, vol. 6, Article 20, 1-10) (Year: 2018).*
Mano, "Features and applications of bilirubin oxidases," Applied Microbiology and Biotechnology, Aug. 3, 2012, vol. 96, pp. 301-307.
Li et al., "Quality catbon fibers from fractionated lignin," Green Chemistry, 2017, vol. 19, pp. 1628-1634.
Zhang et al., "Catalytic Lignin Depolymerization to Aromatic Chemicals," Accounts of Chemical Research, 2020, vol. 53, pp. 470-484.
Sun et al., "Bright Side of Lignin Depolymerization: Toward New Platform Chemicals," Chemical Reviews, 2018, vol. 118, pp. 614-678.
International Search Report, dated Dec. 13, 2018, from corresponding PCT application No. PCT/EP2018/078244.

* cited by examiner

*Primary Examiner* — Liam J Heincer
(74) *Attorney, Agent, or Firm* — ArentFox Schiff LLP

(57) ABSTRACT

Disclosed is a lignin that is soluble in a medium having a pH greater than or equal to 4, a solution containing same, a method for producing same, and uses thereof, in particular for preparing lignin fibers and carbon fibers. Soluble lignin may be obtained by enzymatic modification.

20 Claims, No Drawings

ENZYMATIC MODIFICATION OF LIGNIN FOR SOLUBILIZATION THEREOF, AND USES

The present invention relates to a lignin that is soluble in an aqueous medium at a pH greater than or equal to 4 and typically obtained enzymatically in the absence of an organic solvent, a process for the enzymatic solubilization of lignin and its applications, in particular for the preparation of lignin fibers and carbon fibers.

Carbon fibers may be made from petroleum products. However, it is preferred to avoid using petroleum products for economic and ecological reasons, and their harmful effect on the environment. There is, therefore, an industrial need to develop new precursors of carbon fibers, and, more generally, of carbonaceous materials, which are less expensive and more respectful of the environment.

Lignin is a natural polymer that is available in large quantities, in particular from pulp or cellulose processing plants. Unlike polysaccharides, this phenolic polymer has benefited from little industrial recovery other than "lignosulfonate" applications and energy recovery. The potential applications of lignin are numerous. Lignin offers a very high carbon yield during pyrolysis. Lignin is the main source of aromatic carbon produced in nature. Thus, the possibility of obtaining carbon fibers from lignin is of increasing interest in reducing the cost of materials and no longer using petroleum derivatives. Today's lignins are essentially soluble in organic solvents or alkaline aqueous solutions with a high base concentration (pH>10). Some lignins may be chemically modified and functionalized to give lignosulfonates that are soluble in aqueous solvents of neutral, acidic or slightly basic pH. However, these chemically-modified lignins generally exhibit poor carbon yield during calcination. Lignins, in general, may liquefy, or not, at high temperature. Mistakenly, we speak of fusible or infusible lignin. Fusible lignins may be mixed with thermoplastic polymers to be melt-spun. However, it is critical to stabilize the fibers during calcination due to lignin liquefaction. This makes the process slow, expensive and difficult. Infusible lignins cannot be used in the melt. They may, however, be spun via the solvent route, generally in the presence of a binder polymer, typically of the PVA or cellulose type. However, to date and to the knowledge of the inventors, there is no aqueous pH neutral process for producing lignin fibers.

Patent application EP 2 535 378 describes a lignin soluble in several organic solvents which have a pH of 4 or higher, such as acetone and cyclohexanone.

Patent application EP 2 213 678 relates to a process for dissolving lignin, the product of which is a solubilized lignin. The examples relate to an acetone-water mixture. The lignins according to this patent application contain a great deal of sulfur (water-soluble lignosulfonate) or are non-functionalized lignins (alkali lignin) that are not soluble in water at moderate pH (~between pH 4 and 10). These lignins may only be dissolved in very basic media which contain a very large amount of sodium hydroxide, potassium hydroxide. This is an important constraint for spinning because these bases will end up in the fibers.

U.S. Pat. No. 3,461,082 relates to a process for manufacturing lignin fibers. This is lignin sulfonate which has the disadvantage that the sulfonate groups weaken the mechanical properties of the fibers. In addition, the lignin must be dissolved at 80° C. in NaOH.

US Patent 2015/0037241 application also relates to a process for manufacturing lignin and carbon fibers comprising soluble lignin which is dissolved and coagulated to prepare the fibers. This is a polymeric lignin which is soluble in organic solvent, but not in water with a pH above 4.

Patent application JP H05 336951 relates to a process for the solubilization of lignin with a bacterium.

Thus, the present invention aims to solve the technical problem of providing a precursor of carbonaceous material that is not derived from petroleum, and, more particularly, aims to provide a precursor of natural origin.

The present invention also aims to solve the technical problem of providing a new way of synthesizing carbon fibers.

The present invention also aims to solve the technical problem of limiting the negative impact on the environment of current processes of manufacturing carbon fibers.

The present invention also aims to provide a process for preparing carbon fibers at reduced costs.

Another object of the present invention is to provide a process for the preparation of carbon fibers via the aqueous route.

Another object of the present invention is to provide a process for the preparation of lignin via the aqueous route for its use in the preparation of lignin fibers and/or carbon fibers.

The present invention more particularly aims to solve the technical problem of solubilizing lignin. Even more particularly, the object of the present invention is to solve the technical problem of solubilizing lignin without using an organic solvent.

The present invention makes it possible to solve one or more of the technical problems stated above.

Laccases are copper-based enzymes used to transform lignin enzymatically into high added value aromatic chemicals. However, these enzymes are only active at low pH (below 5). Since lignin is not very soluble in an acid medium, it is necessary to add organic solvents to dissolve it, but to the detriment of the activity of the enzyme.

It has been discovered by the present inventors that it is possible to dissolve lignin at neutral or slightly basic pH, without adding organic solvent to dissolve it. This solubilization may be effected enzymatically.

Thus the present invention relates to a process for the solubilization of lignin comprising bringing a lignin into contact with at least one bilirubin oxidase enzyme (BOD), in the presence or absence of a redox mediator, and obtaining a lignin that is soluble in medium with a pH greater than or equal to 4, preferably greater than or equal to 5, more preferably greater than or equal to 6, and even more preferably greater than or equal to 7. In fact, it has been discovered that enzymes of the bilirubin oxidase type, which are stable and active in an acid medium but also in a neutral and basic medium, make it possible to modify the lignin so as to make it soluble at neutral or basic pH (in particular at pH 5 to 11). In addition, and advantageously, these bilirubin oxidases are more active and more stable than laccases at higher temperatures (up to 70° C.). However, bilirubin oxidases can also function under the conditions used for laccases.

The process according to the invention makes it possible to dissolve the lignin at basic pH, without it precipitating when the pH is lowered. Conversely, the lignin precipitates when using conventional processes if the pH is lowered.

According to one variant, bilirubin oxidase (BOD) may be of fungal origin. According to one embodiment, the BOD used in the context of the present invention is a BOD described in international application WO 2012/160517 (BOD EC 1.3.3.5. of *Magnaporthe oryzae* origin).

According to another variant, the BOD may be of bacterial origin. According to one embodiment, the BOD used in the context of the present invention may be a BOD described in international application WO 2011/117839 (BOD EC 1.3.3.5. of *Bacillus pumilus* origin).

These two international applications WO 2011/117839 and WO 2012/160517 are incorporated here for reference. These two international applications do not, however, cover the solubilization of lignin. They only cover the delignification of the wood pulp. However, these degraded lignins are not optimal for preparing carbon fibers by spinning.

Typically, a process according to the invention comprises the solubilization of lignin in a solution comprising water, and, preferably, a buffering agent. According to a preferred embodiment, the solubilization of lignin takes place in water as the sole solvent, and preferably with a buffering agent.

According to one embodiment, the lignin may be of the kraft (or alkaline lignin) type. We talk about kraft lignin when it is obtained by a kraft process (also known as "kraft pulping" or sulphate process) which is a process of converting wood into pulp. The kraft process involves treating wood chips with a hot mixture of water, sodium hydroxide, and sodium sulfide, breaking down the wood fibers and separating lignin and hemicellulose from cellulose. This technique comprises mechanical and chemical steps, in particular so-called impregnation and cooking.

According to one embodiment, the lignin is of the organosolv type.

For example, a buffering agent may be chosen from a borate, sodium phosphate (NaPi) buffer or any other buffer which makes it possible to maintain a neutral to basic pH.

The lignin dispersed in the solution preferably undergoes an ultrasound treatment so as to fragment the material into small particles which will react better with the enzymes.

Then, bilirubin oxidase is added to this lignin-containing solution in the presence or absence of a redox mediator, and then placed under conditions allowing its enzymatic action on the lignin in order to dissolve it. Typically, bilirubin oxidase is incubated at 37° C., preferably with stirring and a supply of oxygen. Typically, the enzymatic action takes place for 2 to 48 hours, preferably for 10 to 24 hours.

Among the redox mediators, mention may be made, for example, of 2,2-azino-bis-[3-ethylbenzthiazoline-6-sulfonicacid] (ABTS), 2,6-dimethoxyphenol (2,6-DMP), syringaldazine, conjugated or unconjugated bilirubin, or osmium compounds.

According to one embodiment, the lignin obtained after enzymatic treatment preferably undergoes treatment with ultrasound, so as to optimize and accelerate its dissolution, and to denature the enzyme at the end of incubation.

Advantageously, the lignin obtained after enzymatic treatment in aqueous solvent may be separated from the salts, for example by dialysis, or centrifugation.

According to a preferred embodiment, the insolubles may be separated from the soluble lignin, for example by centrifugation. Soluble lignin is present in the supernatant when centrifugation is used.

According to one embodiment, the soluble lignin is lyophilized.

The present invention thus relates to a soluble lignin lyophilisate.

Typically, soluble lignin is soluble in water at a concentration of up to 90% by mass based on the mass of the solution.

The solubility of lignin is assessed at room temperature, preferably in an aqueous solution, typically water, by microscopy and by spontaneous re-dissolution of the lyophilized lignin in an aqueous solvent. No precipitate is observed.

The present invention, therefore, also relates to a water-soluble lignin pH greater than or equal to 4, preferably greater than or equal to 5, more preferably greater than or equal to 6, and even more preferably greater than or equal to 7, and with a pH less than 12, preferably less than 11, and more preferably less than 10.

Advantageously, according to one embodiment, the lignin is infusible.

Advantageously, the soluble lignin is obtained by modification by the enzymatic route. Typically, a soluble lignin obtained via the enzymatic route differs from a soluble lignin obtained via the chemical route by the absence of synthetic impurities of the chemical route and the absence of sulfate or sulfonate groups.

According to one embodiment, the lignin may be soluble at a pH greater than or equal to 7.5, and more preferably at a pH greater than or equal to 8.

According to one embodiment, lignin is soluble over a pH range from 8 to 10.

The lignin according to the invention may be soluble at a lower pH (more acidic).

By infusible is meant that lignin does not liquefy even when heating the material to its calcination temperature, typically for example at 1000° C. This makes it easier to get carbon fiber from the infusible lignin.

According to a preferred variant, the lignin according to the present invention does not comprise a sulfonate group.

According to a variant, the lignin according to the invention has a carbon yield greater than 30%, preferably greater than 35%, and more preferably greater than 39%. The carbon yield is defined as the ratio between the mass of carbon obtained and the mass of initial product after treatment at high temperature and under an inert atmosphere allowing calcination of the initial product.

Very advantageously, according to the invention, lignin is soluble in an aqueous solution, and preferably in water. Thus, the present invention relates to a solution with a pH greater than or equal to 4, preferably greater than or equal to 5, more preferably greater than or equal to 6, and still more preferably greater than or equal to 7, said solution comprising a soluble lignin as defined according to the present invention, or capable of being obtained according to the process defined according to the present invention.

According to one embodiment, the solution of the invention comprises at least 5%, and preferably at least 6%, by mass of soluble lignin relative to the weight of the total mass of the solution.

According to one embodiment, the solvent of the solution comprises or consists of water.

Alternatively, the soluble lignin solution may comprise a water-soluble polymer, for example a water-soluble polysaccharide. Advantageously, the water-soluble polymer may be chosen from the polymers forming the lignin binder for the preparation of lignin fibers.

Advantageously, as water-soluble polymer, we may use an alginate, a polyvinyl alcohol and its derivatives, a lactic acid and its derivatives, a polyacrylamide and its derivatives, a polyacrylic acid and its derivatives, a polyvinylpyrolidone, a polyoxyethylene and its derivatives, a polyurethane and its derivatives.

According to one embodiment, the solution comprises from 0.11 to 40% of soluble lignin and from 0.05 to 20% of a water-soluble polymer, for example of alginate, wherein the percentages are expressed by mass relative to the total mass of the solution.

According to one embodiment, the solution comprises from 0.6 to 20% by mass of lignin and from 0.2 to 2% by mass of alginate.

The invention also relates to a process for the preparation of lignin fibers.

More particularly, the invention relates to the manufacture of lignin fibers, characterized in that it comprises:

preparation of soluble lignin as defined according to the invention, or capable of being obtained according to the process defined according to the invention, bringing the soluble lignin into contact with an aqueous solution, optionally in the presence of a water-soluble polymer, coagulation or crosslinking of lignin, optionally in the presence of the water-soluble polymer, with a coagulating or crosslinking agent, and obtaining lignin fibers.

The preparation of lignin fibers may be carried out according to a conventional process, known to those skilled in the art. Advantageously, according to one embodiment, the present invention makes it possible to use a process for the manufacture of lignin fibers via the aqueous route, i.e. where only water is used as solvent and without adding organic solvent. Thus, the present invention makes it possible to provide a process for manufacturing ecological lignin fibers. Furthermore, a process according to the present invention makes it possible to limit the costs of producing lignin fibers.

According to one embodiment, a water-soluble polymer forming a lignin binder for the manufacture of lignin fibers is added to the solution containing the soluble lignin. We may, for example, prepare a solution as described above comprising a water soluble polymer and soluble lignin.

For example, said solution comprising a water-soluble lignin and a water-soluble binder may be brought into contact with a crosslinking or coagulating agent to form lignin fibers.

As a crosslinking or coagulating agent, it is possible, for example, to use a calcium salt, but other divalent cations ($Mg^{2+}$, $Mn^{2+}$, $Ba^{2+}$, $Cu^{2+}$, boric acid and borate salts, sodium sulfate, solvents organic, . . . ) may be used. Advantageously, to limit the negative impact on the environment, calcium chloride may be used as the crosslinking agent with alginate as a binder. Typically, the solution containing lignin and the binder is injected into a solution containing a crosslinking or coagulating agent, to form lignin fibers.

The invention, therefore, also relates to lignin fibers comprising a soluble lignin as defined according to the invention or capable of being obtained according to the process defined according to the invention and at least one polymer soluble in water.

According to one embodiment, the lignin fibers comprise an alginate.

Advantageously, according to one embodiment, the lignin fibers comprise a mass concentration of lignin greater than or equal to 60%, and preferably greater than or equal to 90% in the lignin fiber.

According to one embodiment, the lignin fiber comprises a mass concentration of lignin greater than or equal to 70%, and preferably greater than or equal to 80% in the lignin fiber.

Advantageously, the present invention also makes it possible to provide a process for the continuous extrusion of lignin fibers. This process makes it possible to supply lignin fibers in single or multi filaments, which are homogeneous, reproducible, and of controlled diameter.

When a mixed solution (for example lignin in a water/acetone mixture) is used for spinning, the inventors discovered that it was not possible to properly spin the lignin fibers. Advantageously, with a process according to the invention, precipitation is obtained in the coagulation bath.

According to one embodiment, the solution of the mixture (lignin/soluble polymer) is extruded by injecting a quantity of solution at a flow rate varying from 2 to 20 ml/h and even more preferably from 8 to 15 ml/h in a coagulation bath containing at least one crosslinking agent (for example a calcium salt). The diameter of the injection nozzle may generally vary between 50 and 500 μm, whether in single or multiple filaments. The solidification of the fiber within the coagulation bath is very rapid and takes place almost immediately after the injection of the solution. However, in order to optimize the contact time and reinforce the strength of the fibers, it is important to control the injection rate and the speed of extraction of the fiber from the coagulation bath. Thus, the contact time of the solution in the coagulation bath typically varies from 10 seconds to approximately 5 minutes. According to one embodiment, the extraction of the fiber outside the coagulation bath is also carried out continuously at a speed varying from 0.5 to 3 m/min. The composite lignin fiber is then continuously washed in a washing bath preferably comprising water, at a speed varying for example from 0.5 to 3 m/min. According to one variant, the duration of the washing step, i.e. the duration of bringing the composite lignin fibers into contact with the washing bath is at least 1 minute, wherein this duration preferably varies from 1 to 3 minutes. The step of drying the composite lignin fibers may, for example, be carried out by exposing said fibers to a temperature varying from 50 to 90° C., and even more preferably from 60 to 70° C. The duration of the drying step may, for example, vary from approximately 1 to 5 minutes as a function of the drying temperature used. According to a preferred embodiment of the invention, the drying step may be carried out by continuous passage of the composite lignin fibers between lamps emitting infrared radiation, or else by passage through the enclosure of a preferably circulating gas oven at a speed of 1 to 8 m/min.

Controlling the extraction speeds of the composite fiber at each manufacturing step, advantageously makes it possible to produce lignin fibers in a reproductive manner and of controlled diameter. In addition, thanks to the controlled stretch rates that the composite fiber undergoes during its production, it is possible to modify its physical properties.

The dried composite lignin fibers may, for example, be used as raw material and take the form of continuous monofilaments, short or staple fibers, yarns or woven fabrics, or any other suitable form of fibers.

Lignin fibers may be used for different applications. For example, lignin fibers may be used in the cosmetics and food industries, as additives for cement, or to form emulsions, for example for the preparation of asphalt. Lignin fibers may, in particular, be used for the manufacture of carbon fibers.

Advantageously, the lignin fibers obtained have a high concentration of lignin.

The mechanical properties of interest are the Young's modulus, breaking strength, elongation at break, electrochemical capacitance, porosity, electronic and thermal conductivity.

The invention, therefore, also relates to a process for preparing carbon fibers comprising the calcination of a lignin fiber as defined according to the invention, or capable of being obtained according to the process defined according to the invention.

According to one embodiment, the process for manufacturing carbon fibers by the aqueous route comprises:

- the preparation of soluble lignin as defined according to the invention or capable of being obtained according to the process defined according to the invention,
- bringing the soluble lignin into contact with an aqueous solution, optionally in the presence of a water-soluble polymer,
- coagulation or crosslinking of lignin with a coagulating or crosslinking agent, obtaining lignin fibers,
- possibly washing with water and drying the lignin fibers,
- calcination of lignin fibers, and
- obtaining carbon fibers.

The calcination is typically carried out at a temperature above 700° C., and, for example, at 1000° C. under an inert atmosphere. Above a certain temperature, the fibers may be graphitized. This temperature is generally above 2000° C.

The invention, therefore, also relates to carbon fibers capable of being obtained by a process as described in the present invention. Advantageously, the carbon fibers obtained may be bio-sourced, and have a low production cost.

The carbon fibers according to the invention offer chemical resistance, heat resistance, electrical conductivity and textile flexibility, which are advantageous for industrial applications in various fields. It is possible, for example, to use the carbon fibers according to the invention in the automobile industry, as a filler for plastics, as a filtering material, as a material for removing gas dust at high temperature, as an electrically resistant material, as an electrode, as packaging material, in composite materials for aeronautics, space, automotive, sport and, generally, any structure that must combine lightness and high mechanical strength. etc.

To date, there are no commercial carbon fibers made from enzymatically-modified lignin.

The present invention makes it possible to supply carbon fibers resulting from an ecological process, using no organic solvent, in particular no toxic solvent, nor precursors derived from petroleum. The present invention provides a process for preparing carbon fibers from an aqueous process.

Advantageously, since the lignin fibers according to the present invention are not fusible, the difficult stabilization operation may be avoided during calcination for the preparation of carbon fibers.

The invention, therefore, represents a significant advance in terms of the costs of manufacturing lignin fibers and carbon fibers, on the one hand, and for its environmentally friendly aspect, on the other hand.

By dissolving the infusible lignin, the invention also makes it possible to provide an aqueous process offering a high carbon yield, and allows the preparation of a highly concentrated solution in water. Advantageously, a lignin according to the present invention makes it possible to obtain high levels of carbon during calcination.

The term "according to the invention" defines any of the embodiments, variants, and advantageous or preferred characteristics, taken alone or in any of their combinations.

Other objects, characteristics and advantages of the invention will become apparent to those skilled in the art after reading the explanatory description which refers to examples which are given only by way of illustration and which do not in any way limit the scope of the invention.

The examples form an integral part of the present invention and any characteristic which appears new compared with any prior art from the description taken as a whole, including the examples, forms an integral part of the invention in its function and in its generality.

Thus, each example is general in scope.

On the other hand, in the examples, all the percentages are given by mass unless otherwise indicated, the temperature is that of ambient 20-25° C. and is expressed in degrees Celsius unless otherwise indicated, while the pressure is atmospheric pressure (101325 Pa) unless otherwise indicated.

EXAMPLES

Example 1a—Solubilization of Lignin with a Purified Enzyme 2 g of kraft lignin, purchased from Sigma-Aldrich under the reference (370959) are taken up in 100 ml of 50 mM Borate pH9 buffer and sonicated for 30 min under the following conditions: amplitude 20%, 0.5 s ON, 0.5 s OFF (Branson).

5.4 mg of BOD of *Bacillus pumilus* are then added to this solution at 37° C. with stirring with a magnetic bar at 100 rpm and a bubbling of compressed air at 0.1 $l/min^{-1}$, for 16 hours. The solution is then sonicated for 30 min under the conditions described above, and then dialyzed in a 100 ml 10 kDa dialysis rod, in three 4 l baths of mQ water, the first of 2 hours, the second of 4 hours, and the third for the night. The solution is centrifuged for 5 minutes at 1500 rpm. The supernatant containing soluble lignin is lyophilized overnight and stored at room temperature.

Example 1b—Solubilization of Lignin with an Unpurified Enzyme 2 g of kraft lignin, purchased from Sigma-Aldrich under the reference (370959) are taken up in 100 ml of 50 mM Borate pH9 buffer and sonicated for 30 min under the following conditions: amplitude 20%, 0.5 s ON, 0.5 s OFF (Branson).

20 g of *E. coli* Origami B DE3 pellet containing the BOD of *Bacillus pumilus*, obtained as described in Gounelle et al. (J. Biotechnol, 19-25 2016), is resuspended in 120 ml of Borate pH9. The bacteria are comminuted by 3 passages in a cell mill (Constant Systems Ltd, CellD) at 2200 bar. The solution is centrifuged at 21,000 g for 1 hour and the supernatant is filtered at 0.22 μm and stored in a 20 ml aliquot at −80° C.

20 ml of supernatant containing the BOD of *Bacillus pumilus*, previously prepared, are added to the lignin solution at 37° C. with stirring with a magnetic bar at 100 rpm and bubbling with compressed air at 0.1 $l/min^{-1}$ for 16 hours. The solution is then sonicated for 30 min under the conditions described above, and then dialyzed in a 100 ml 10 kDa dialysis unit, in three 4 l baths of mQ water, the first of 2 hours, the second of 4 hours, and the third for the night. The solution is centrifuged for 5 minutes at 1500 rpm. The supernatant containing soluble lignin is lyophilized overnight and stored at room temperature.

Example 2—Manufacture of Composite Lignin Fibers

The lyophilized lignin obtained in Example 1 is resolubilized in water. Sodium alginate (Protanal LF200 FTS, FMC Corporation) is added to obtain a homogeneous, aqueous solution containing 5.67% by mass of lignin and 0.66% by mass of alginate. This solution is then injected, at a speed of 12 ml/h into a coagulation bath containing a solution of 100 mM of calcium chloride, using a syringe pump and a 300 μm nozzle. The coagulated fiber is then removed continuously at a speed of 1.3 m/min, then continuously rinsed in a tank for washing with distilled water at a speed of 1.7 m/min. The washed composite lignin fiber is then dried at 60° C. in an infrared oven at 1.7 m/min and then directly formed into a coil at a speed of 1.8 m/min. At the end of the manufacturing process, a homogeneous lignin fiber is obtained at a mass concentration of 90.9% lignin.

Example 3—Preparation of Carbon Fibers

Lignin fibers obtained according to Example 2 are used in this example.

A carbon fiber is obtained after calcination under an inert atmosphere of this fiber at 1000° C. (temperature rise of 5° C./min and a plateau of 30 min). Since the lignin used is infusible, it is not necessary to carry out a stabilization treatment for carbonization, thus making the process even less expensive and faster than the processes with fusible lignin.

Such a process according to Examples 1 to 3 is easily transposable to the industrial scale.

Example 4 (Comparative)—Use of Mixed Lignin Solutions (Water+Acetone) for Spinning The same percentages of lignin and alginate as in Example 2 were resolubilized in solutions containing 5, 25, 50, 90% acetone. Under these conditions, it was impossible to obtain coagulation of the fiber in a 100 mM calcium chloride bath, thus showing the need to resolubilize the mixture exclusively in water.

The invention claimed is:

1. A lignin soluble in water throughout a pH range from 5 to 12, wherein said soluble lignin is obtained by the action of at least one bilirubin oxidase enzyme (BOD) classified as E.C. 1.3.3.5 by aqueous route where only water is used as solvent, wherein said soluble lignin does not comprise sulfate or sulfonate groups.

2. The soluble lignin according to claim 1, wherein said lignin is infusible.

3. The soluble lignin according to claim 1, wherein said lignin is a lyophilizate.

4. The lignin according to claim 1, wherein said lignin is soluble in water at a pH greater than or equal to 7.

5. The lignin according to claim 1, wherein said lignin is soluble in water at a pH less than 10.

6. A process for the solubilization of lignin wherein said process comprises bringing a lignin wherein said process comprises bringing a lignin into contact with at least one bilirubin oxidase enzyme (BOD) classified as E.C. 1.3.3.5, in the presence or absence of a redox mediator, wherein the solubilization of lignin takes place in water as a sole solvent, and obtaining a lignin that is soluble in water throughout a pH range from 5 to 12, wherein said soluble lignin does not comprise sulfate or sulfonate groups.

7. The process according to claim 6, wherein said lignin is soluble in water at a pH, greater than or equal to 7.

8. A solution with a pH greater than or equal to 5 comprising a lignin soluble in water throughout a pH range from 5 to 12, wherein said soluble lignin is obtained by the action of at least one bilirubin oxidase enzyme (BOD) classified as E.C. 1.3.3.5 by aqueous route where only water is used as solvent, wherein said soluble lignin does not comprise sulfate or sulfonate groups.

9. The solution according to claim 8, wherein said solution comprises at least 5% by mass of soluble lignin relative to the weight of the total mass of the solution.

10. The solution according to claim 8 wherein said solution comprises a water-soluble polymer, and, for example, a water-soluble polysaccharide, and more particularly alginate.

11. Fibers comprising a lignin soluble in water throughout a pH range from 5 to 12, wherein said soluble lignin is obtained by the action of at least one bilirubin oxidase enzyme (BOD) classified as E.C. 1.3.3.5 by aqueous route where only water is used as solvent, wherein said soluble lignin does not comprise sulfate or sulfonate groups, and at least one polymer that is soluble in water.

12. The fibers according to claim 11, wherein said fibers comprise an alginate.

13. The fibers according to claim 11, wherein said fibers comprise a mass concentration of lignin greater than or equal to 60 in the lignin fiber.

14. The fibers according to claim 11, wherein said lignin is soluble in water at a pH greater than or equal to 7.

15. The process for manufacturing carbon fibers, wherein said process comprises the calcination of lignin fibers as defined in claim 13.

16. A process for the production of lignin fibers by aqueous route, wherein said process comprises:

- preparing lignin soluble in water throughout a pH range from 5 to 12, wherein said soluble lignin is obtained by the action of at least one bilirubin oxidase enzyme (BOD) classified as E.C. 1.3.3.5 by aqueous route where only water is used as solvent, wherein said soluble lignin does not comprise sulfate or sulfonate groups and wherein only water is used as solvent,
- bringing the soluble lignin into contact with an aqueous solution, optionally in the presence of a water-soluble polymer, coagulation or crosslinking of lignin, optionally in the presence of the water-soluble polymer, with a coagulating or crosslinking agent, and
- obtaining lignin fibers,
- wherein said process is conducted in the absence of organic solvent.

17. The process for the production of lignin fibers according to claim 16, wherein said lignin is soluble in water at a pH greater than or equal to 7.

18. A process for manufacturing carbon fibers by aqueous process, wherein said process comprises:

- preparing lignin soluble in water throughout a pH range from 5 to 12, wherein said soluble lignin is obtained by the action of at least one bilirubin oxidase enzyme (BOD) classified as E.C. 1.3.3.5 by aqueous route where only water is used as solvent, wherein said soluble lignin does not comprise sulfate or sulfonate groups,
- bringing the soluble lignin into contact with an aqueous solution, optionally in the presence of a water-soluble polymer,
- coagulation or crosslinking of lignin with a coagulating or crosslinking agent,
  - obtaining lignin fibers,
  - possibly washing with water and then drying the lignin fibers,
  - calcining said lignin fibers, and
  - obtaining carbon fibers, wherein said process is conducted in the absence of organic solvent.

19. The process for manufacturing carbon fibers by aqueous process according to claim 18, wherein said lignin is soluble in water at a pH greater than or equal to 7.

20. The process for manufacturing carbon fibers by aqueous process according to claim 18, wherein said lignin is soluble in water at a pH less than 10.

* * * * *